US010795162B2

(12) United States Patent
Cho

(10) Patent No.: US 10,795,162 B2
(45) Date of Patent: Oct. 6, 2020

(54) IMAGE DISPLAYABLE EYEGLASSES

(71) Applicant: FUJIFILM Corporation, Tokyo (JP)

(72) Inventor: Michio Cho, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/218,498

(22) Filed: Dec. 13, 2018

(65) Prior Publication Data

US 2019/0113758 A1 Apr. 18, 2019

Related U.S. Application Data

(63) Continuation of application No. PCT/JP2017/011026, filed on Mar. 17, 2017.

(30) Foreign Application Priority Data

Jun. 27, 2016 (JP) .................. 2016-126602

(51) Int. Cl.
*G02B 27/01* (2006.01)
*G02F 1/13* (2006.01)
(Continued)

(52) U.S. Cl.
CPC ............ *G02B 27/0172* (2013.01); *A61B 3/00* (2013.01); *G02B 23/125* (2013.01); *G02B 27/04* (2013.01);
(Continued)

(58) Field of Classification Search
CPC .. G02B 27/0172; G02B 30/34; G02B 23/125; G02B 27/04; G02B 2027/0134;
(Continued)

(56) References Cited

U.S. PATENT DOCUMENTS

2001/0028482 A1 10/2001 Nishioka
2001/0055208 A1* 12/2001 Kimura ................ G02B 26/001
362/260
(Continued)

FOREIGN PATENT DOCUMENTS

JP H11327750 11/1999
JP 2001209037 8/2001
(Continued)

OTHER PUBLICATIONS

"International Search Report (Form PCT/ISA/210) of PCT/JP2017/011026," dated Jun. 20, 2017, with English translation thereof, pp. 1-5.

(Continued)

*Primary Examiner* — Md Saiful A Siddiqui
(74) *Attorney, Agent, or Firm* — JCIPRNET

(57) ABSTRACT

The image displayable eyeglasses include: a first transmissive optical element 13 that transmits an image of a subject and is capable of changing a refractive power; and a second transmissive optical element 13 that displays or reflects an image using an image signal and transmits the image of the subject. The image displayable eyeglasses are capable of switching between an image display mode, in which the image is displayed or reflected by the second transmissive optical element 12 so as to be incident on eyes of a wearer of the eyeglass body, and an eyeglass mode, in which the image of the subject transmitted through the first transmissive optical element 12 and the second transmissive optical element 13 is incident on the eyes of the wearer. The first transmissive optical element 12 is disposed closer to the wearer than the second transmissive optical element 13.

20 Claims, 8 Drawing Sheets

(51) Int. Cl.
    *G02B 27/22* (2018.01)
    *G02B 27/04* (2006.01)
    *A61B 3/00* (2006.01)
    *G03H 1/08* (2006.01)
    *G02B 23/12* (2006.01)
    *G03H 1/22* (2006.01)
    *G02B 30/34* (2020.01)
    *G02C 7/08* (2006.01)

(52) U.S. Cl.
    CPC ............ *G02B 30/34* (2020.01); *G02F 1/13* (2013.01); *G03H 1/0808* (2013.01); *G03H 1/2294* (2013.01); *G02B 2027/0118* (2013.01); *G02B 2027/0134* (2013.01); *G02B 2027/0138* (2013.01); *G02B 2027/0174* (2013.01); *G02B 2027/0178* (2013.01); *G02C 7/083* (2013.01); *G02C 7/086* (2013.01); *G02C 2202/22* (2013.01); *G03H 2225/32* (2013.01); *G03H 2270/55* (2013.01)

(58) Field of Classification Search
    CPC .... G02B 2027/0118; G02B 2027/0138; G02B 2027/0174; G02B 2027/0178; A61B 3/00; G03H 1/0808; G03H 1/2294; G03H 2225/32; G03H 2270/55; G02F 1/13; G02C 7/086; G02C 7/083; G02C 2202/22
    See application file for complete search history.

(56) References Cited

U.S. PATENT DOCUMENTS

| | | | | |
|---|---|---|---|---|
| 2002/0016629 | A1* | 2/2002 | Sandstedt | G02B 27/0025 623/6.11 |
| 2004/0120035 | A1* | 6/2004 | Hoffmann | G02C 7/081 359/407 |
| 2006/0023278 | A1 | 2/2006 | Nishioka | |
| 2008/0088756 | A1* | 4/2008 | Tseng | G02B 1/06 349/33 |
| 2008/0211978 | A1 | 9/2008 | Hikmet et al. | |
| 2010/0103204 | A1* | 4/2010 | Shibata | G09G 3/3406 345/690 |
| 2012/0050141 | A1* | 3/2012 | Border | G02B 27/017 345/8 |
| 2015/0148396 | A1* | 5/2015 | Zanella | A61K 9/0024 514/401 |
| 2015/0234187 | A1 | 8/2015 | Lee | |
| 2016/0033934 | A1* | 2/2016 | Kim | G03H 1/0808 359/9 |
| 2016/0180780 | A1* | 6/2016 | Chen | G09G 3/2003 345/207 |
| 2016/0379606 | A1* | 12/2016 | Kollin | G02B 27/0093 345/428 |
| 2017/0273564 | A1* | 9/2017 | Banke | A61B 5/7221 |
| 2017/0307890 | A1* | 10/2017 | Wang | G02C 7/022 |
| 2018/0152694 | A1* | 5/2018 | Oonishi | H04N 13/117 |

FOREIGN PATENT DOCUMENTS

| | | |
|---|---|---|
| JP | 2002098928 | 4/2002 |
| JP | 2005172851 | 6/2005 |
| JP | 2006126590 | 5/2006 |
| JP | 2008083289 | 4/2008 |
| JP | 2009500671 | 1/2009 |
| JP | 2013097283 | 5/2013 |

OTHER PUBLICATIONS

"Written Opinion of the International Searching Authority (Form PCT/ISA/237) of PCT/JP2017/011026," dated Jun. 20, 2017, with English translation thereof, pp. 1-12.

* cited by examiner

IMAGE DISPLAYABLE EYEGLASSES

CROSS-REFERENCE TO RELATED APPLICATIONS

This application is a Continuation of PCT International Application No. PCT/JP2017/011026 filed on Mar. 17, 2017, which claims priority under 35 U.S.C. § 119(a) to Patent Application No. 2016-126602 filed in Japan on Jun. 27, 2016, all of which are hereby expressly incorporated by reference into the present application.

BACKGROUND OF THE INVENTION

1. Field of the Invention

The present invention relates to image displayable eyeglasses for allowing a wearer to see images displayed or projected on eyeglass lenses.

2. Description of the Related Art

In the related art, various types of transmissive eyeglass type display devices to be worn on a head have been proposed. For example, in JP2008-083289A, an eyeglass type display device has been proposed in which an image of the front view of a wearer is captured by an imaging unit and the image is displayed on an eyeglass type display unit.

In the eyeglass type display device disclosed in JP2008-083289A, it is proposed to enlarge the image displayed on the display unit and set the display unit to a transmissive state.

In addition, in JP2002-098928A, an eyeglass type display device, which guides an image displayed on a display unit through a plate-like member and reflects the image toward eyes of the wearer through a hologram element provided in the plate-like member, has been proposed. In JP2002-098928A, it has been proposed to provide the plate-like member with optical power.

SUMMARY OF THE INVENTION

However, since the transmissive state of the eyeglass type display device described in JP2008-083289A merely controls the display unit such that the display unit is in the transmissive state. Therefore, in a case where a wearer is for example myopic or hyperopic, it is not possible to clearly see the front view.

In addition, in JP2002-098928A, as described above, it is proposed to give optical power to the plate-like member, but since this optical power is fixed, it is not possible to change in accordance with the visual acuity of a wearer. Further, in the eyeglass type display device of JP2002-098928A, even in a case where the wearer is able to clearly see the front view of the wearer, it is not possible to correct the visibility of the virtual image formed by the hologram element.

The present invention has been made in view of the above problems, and it is an object of the present invention to provide image displayable eyeglasses that have an image display function and an eyeglass function and that are capable of changing the refractive power in accordance with visual acuity of a wearer and the like and further capable of correcting visibility of the image reproduced through the image display function.

First image displayable eyeglasses according to the present invention comprise: an eyeglass body; a first transmissive optical element that transmits an image of a subject and is capable of changing a refractive power; a second transmissive optical element that displays or reflects an image using an image signal and transmits the image of the subject; and a control unit that performs control capable of switching between an image display mode, in which the image is displayed or reflected by the second transmissive optical element so as to be incident on eyes of a wearer of the eyeglass body, and an eyeglass mode, in which the image of the subject transmitted through the first transmissive optical element and the second transmissive optical element is incident on the eyes of the wearer. The first transmissive optical element is disposed closer to the wearer than the second transmissive optical element.

In the first image displayable eyeglasses of the present invention, a liquid crystal lens may be used as the first transmissive optical element.

In the first image displayable eyeglasses according to the present invention, the liquid crystal lens may have a plurality of divided regions and may be capable of changing a refractive index for each of the divided regions.

The first image displayable eyeglasses according to the present invention may further comprise a third optical element that is disposed closer to the subject than the second transmissive optical element and is capable of switching between a transmission mode, in which light forming the image of the subject is transmitted, and a blocking mode, in which the light forming the image of the subject is blocked. The control unit may control the third optical element such that the third optical element is set in the blocking mode in a case of the image display mode and controls the third optical element such that the third optical element is set in the transmission mode in a case of the eyeglass mode.

The first image displayable eyeglasses according to the present invention may further comprise a third optical element that is disposed closer to the subject than the second transmissive optical element and is capable of switching between a transmission mode, in which light forming the image of the subject is transmitted, and a semi-transmission mode, in which a part of the light forming the image of the subject is blocked. The control unit may control the third optical element such that the third optical element is set in the semi-transmission mode in a case of the image display mode and controls the third optical element such that the third optical element is set in the transmission mode in a case of the eyeglass mode.

In the first image displayable eyeglasses according to the present invention, the control unit may control the third optical element such that the third optical element is set in the transmission mode in a case where a power supply is turned off.

The first image displayable eyeglasses according to the present invention may further comprise a refractive power information acquisition unit that acquires refractive power information of the first transmissive optical element. The control unit may control the refractive power of the first transmissive optical element by using the refractive power information which is acquired by the refractive power information acquisition unit.

In the first image displayable eyeglasses according to the present invention, a plurality of fixed focal length lenses having different refractive powers may be configured to be interchangeable on a side close to the wearer in the first transmissive optical element.

In the first image displayable eyeglasses according to the present invention, a phase modulation computer hologram display element may be used as the second transmissive optical element.

In the first image displayable eyeglasses according to the present invention, the phase modulation computer hologram display element may have a plurality of display pixels.

In the first image displayable eyeglasses according to the present invention, the phase modulation computer hologram display element may display a computer hologram interference pattern using the image signal.

In the first image displayable eyeglasses according to the present invention, the phase modulation computer hologram display element may reproduce the image as a plane image at a position distant from the phase modulation computer hologram display element.

The first image displayable eyeglasses according to the present invention may further comprise a reference light irradiation unit that irradiates the phase modulation computer hologram display element with reference light.

In the first image displayable eyeglasses of the present invention, a thin hologram element may be used as the phase modulation computer hologram display element.

In the first image displayable eyeglasses according to the present invention, a wavelength selective reflection member may be provided on a side close to the subject of the thin hologram element. In addition, the wavelength selective reflection member may reflect the reference light and transmit light having a wavelength other than a wavelength of the reference light.

In the first image displayable eyeglasses according to the present invention, the reference light irradiation unit may irradiate the phase modulation computer hologram display element with three types of reference light having different wavelengths in a time division manner. In addition, the phase modulation computer hologram display element may display a computer hologram interference pattern corresponding to the reference light of each wavelength in a time division manner.

In the first image displayable eyeglasses according to the present invention, the reference light irradiation unit may irradiate the phase modulation computer hologram display element with three types of reference light having different wavelengths simultaneously. In addition, the phase modulation computer hologram display element may display a computer hologram interference pattern obtained by simulating multiple exposures of the three types of reference light.

In the first image displayable eyeglasses according to the present invention, the control unit may turn off the reference light irradiation unit in the case of the eyeglass mode, and may turn on the reference light irradiation unit in the case of the image display mode.

In the first image displayable eyeglasses according to the present invention, the reference light irradiation unit may irradiate the phase modulation computer hologram display element with the reference light which is linearly polarized.

In the first image displayable eyeglasses according to the present invention, the control unit may uniformly control a refractive index of the second transmissive optical element in the case of the eyeglass mode.

The first image displayable eyeglasses according to the present invention may further comprise a distance information acquisition unit that acquires information about a distance between the wearer and the subject. The control unit may control a refractive power of the first transmissive optical element by using the information about the distance acquired by the distance information acquisition unit.

In the first image displayable eyeglasses according to the present invention, the control unit may uniformly control refractive indices of the first transmissive optical element and the second transmissive optical element in a case where a power supply is turned off.

In the first image displayable eyeglasses according to the present invention, the first transmissive optical element may have two liquid crystal layers whose alignment directions are orthogonal to each other.

In the first image displayable eyeglasses according to the present invention, the first transmissive optical element may have two liquid crystal layers having the same alignment direction, and a half wave plate may be provided between the two liquid crystal layers.

In the first image displayable eyeglasses according to the present invention, the first transmissive optical element may have a plurality of pairs of the two liquid crystal layers.

In the first image displayable eyeglasses according to the present invention, the control unit may control the first transmissive optical element such that the first transmissive optical element generates a phase distribution for correcting abnormality of wavefront aberration of each eye.

In the first image displayable eyeglasses according to the present invention, the control unit may acquire information about a brightness of surrounding environment of the wearer and may switch from the eyeglass mode to the image display mode in a case where the brightness is equal to or less than a preset first threshold value.

In the first image displayable eyeglasses according to the present invention, the control unit may perform switching from the eyeglass mode to the image display mode in a case where the brightness is equal to or less than a second threshold value smaller than the first threshold value in a state where the brightness is set in the eyeglass mode so as to be greater than the first threshold value, and may perform switching from the image display mode to the eyeglass mode in a case where the brightness is greater than a third threshold value greater than the first threshold value in a state where the brightness is set in the image display mode so as to be equal to or less than the first threshold value.

In the first image displayable eyeglasses according to the present invention, the control unit may change a transmittance of the light forming the image of the subject through the third optical element continuously or stepwise in a case where the brightness is between the first threshold value and the second threshold value and in a case where the brightness is between the first threshold value and the third threshold value.

In the first image displayable eyeglasses according to the present invention, the control unit may perform control in an intermediate mode, in which the image is displayed by the second transmissive optical element and the image of the subject transmitted through the first transmissive optical element and the second transmissive optical element is made to be incident on the eyes of the wearer, in a case where the brightness is between the first threshold value and the second threshold value and in a case where the brightness is between the first threshold value and the third threshold value.

The first image displayable eyeglasses according to the present invention may further comprise an imaging unit that captures the image of the subject and outputs the image signal.

Further, in the first image displayable eyeglasses according to the present invention, the imaging unit may have a zooming function.

Second image displayable eyeglasses according to the present invention comprise: an eyeglass body; a transmissive optical element that transmits an image of a subject, is capable of changing a refractive power, and displays an image using an image signal; and a control unit that performs control capable of switching between an image display mode, in which the image is displayed by the transmissive optical element so as to be incident on eyes of a wearer of the eyeglass body, and an eyeglass mode, in which the image of the subject transmitted through the transmissive optical element is incident on the eyes of the wearer.

According to the first image displayable eyeglasses of the present invention, the image displayable eyeglasses comprises: a first transmissive optical element that transmits an image of a subject and is capable of changing a refractive power; and a second transmissive optical element that displays or reflects an image using an image signal and transmits the image of the subject. In addition, the image displayable eyeglasses are capable of switching between an image display mode, in which the image is displayed or reflected by the second transmissive optical element so as to be incident on eyes of a wearer of the eyeglass body, and an eyeglass mode, in which the image of the subject transmitted through the first transmissive optical element and the second transmissive optical element is incident on the eyes of the wearer.

Therefore, the image displayable eyeglasses have both the image display function and the eyeglass function and are capable of changing the refractive power in accordance with visual acuity of a wearer and the like.

Further, the first transmissive optical element is disposed closer to the wearer than the second transmissive optical element. Therefore, the visibility of the image reproduced through the image display function can also be corrected.

According to the second image displayable eyeglasses of the present invention, the image displayable eyeglasses comprise: an eyeglass body; and a transmissive optical element that transmits an image of a subject, is capable of changing a refractive power, and displays an image using an image signal. The image displayable eyeglasses are capable of switching between an image display mode, in which the image is displayed by the transmissive optical element so as to be incident on eyes of a wearer of the eyeglass body, and an eyeglass mode, in which the image of the subject transmitted through the transmissive optical element is incident on the eyes of the wearer. Therefore, the image displayable eyeglasses have both the image display function and the eyeglass function and are capable of changing the refractive power in accordance with visual acuity of a wearer and the like.

DESCRIPTION OF THE PREFERRED EMBODIMENTS

Figure 1:
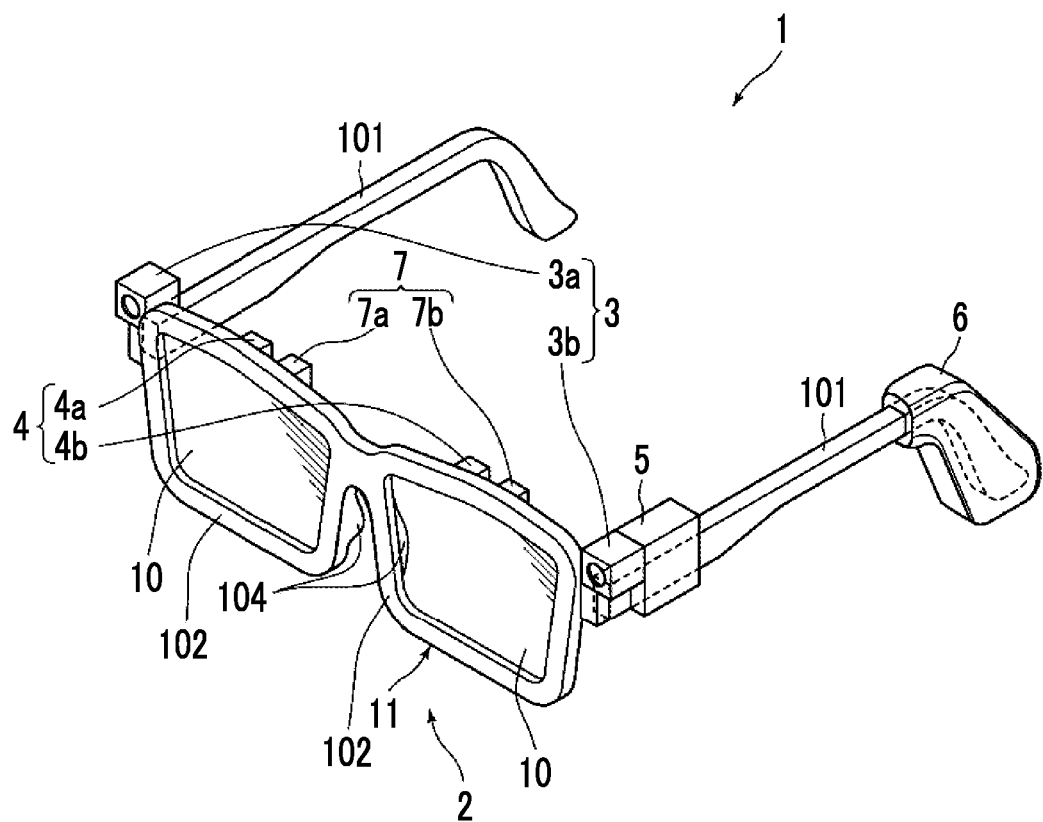
FIG. 1 is a perspective view illustrating a schematic configuration of image displayable eyeglasses according to an embodiment of the present invention.

Hereinafter, image displayable eyeglasses 1 according to an embodiment of the present invention will be described in detail with reference to the drawings. FIG. 1 is a perspective view illustrating a schematic configuration of the image displayable eyeglasses 1 of the present embodiment. In the present specification, the terms "front", "rear", "left", "right", "upper" and "lower" respectively indicate "front", "rear", "left", "right", "upper", and "lower" directions as viewed from a wearer in a state where the image displayable eyeglasses are worn on the wearer's head.

The image displayable eyeglasses 1 (hereinafter simply referred to as eyeglasses 1) according to the present embodiment have an image display function. The image displayable eyeglasses 1 display or project images within the field of view of the wearer of the eyeglasses 1 captured by imaging units on lens units of the eyeglasses 1, and display virtual images on the wearer by causing the light displayed or reflected by the lens units to be incident on the eyes of the wearer. Further, the eyeglasses 1 have an eyeglass function, and are configured to be able to adjust diopter in accordance with visual acuity of the wearer.

Specifically, as shown in FIG. 1, the eyeglasses 1 of the present embodiment comprises a eyeglass body 2 to be mounted on a head of a wearer, an imaging unit 3, a reference light irradiation unit 4, a control board unit 5, a power supply unit 6, and a sight line detection unit 7.

The eyeglass body 2 comprises a frame 11 and two lens units 10 mounted on the frame 11. The frame 11 is composed of temples 101 to be worn by wearer's ears, rims 102 connected to the temples 101 through hinges, a bridge 103 connecting the left and right rims 102, and nose pads 104.

An imaging unit 3 is provided for the eyeglass body 2. The imaging unit 3 is composed of, for example, charge coupled device (CCD) image sensors, complementary metal oxide semiconductor (CMOS) image sensors, optical lenses, and the like. The imaging unit 3 comprises a first camera 3a provided on the temple 101 on the right side and a second camera 3b provided on the temple 101 on the left side. The first camera 3a and the second camera 3b capture images of a subject included in the field of view of the wearer of the eyeglasses 1 and output image signals.

The first camera 3a and the second camera 3b are not limited to be provided on the temples 101, and may be provided on the left and right rims 102, respectively. Further, the cameras may be embedded in the rims 102 of the eyeglass body 2 and the temples 101 so as to be integrated therein. In addition, the first camera 3a and the second camera 3b may be configured to be attachable to and detachable from the eyeglass body 2.

A reference light irradiation unit 4 is provided on the upper sides of the left and right rims 102 of the eyeglass body 2. The reference light irradiation unit 4 comprises a first light source unit 4a provided on the upper side of the right rim 102 and a second light source unit 4b provided on the upper side of the left rim 102. The first light source unit 4a and the second light source unit 4b each irradiate reference light to a second transmissive optical elements 13, which will be described later, provided in each lens unit 10. The first light source unit 4a and the second light source unit 4b each irradiate the second transmissive optical element 13 consisting of the phase modulation computer hologram display element with the reference light. Accordingly, images, which are reproduced by using the images captured by the imaging unit 3, are formed by the second transmissive optical elements 13, and are incident on the eyes of the wearer.

More specifically, the first light source unit 4a and the second light source unit 4b of the present embodiment each sequentially irradiate the second transmissive optical element 13 with three-color reference light beams of green (G), blue (B), and red (R) in a time division manner. The first light source unit 4a and the second light source unit 4b each comprise semiconductor light emitting elements such as a red light emitting diode (LED), a green LED, and a blue LED, but the light source is not limited thereto. It should be noted that the reference light irradiation unit 4 turns off the reference light in a case of an eyeglass mode to be described later and turns on the reference light in a case of an image display mode. By turning off the reference light in the case of the eyeglass mode, it is possible to prevent extra scattered light from occurring and to prevent electric power from being consumed.

Further, it is desirable that the reference light is linearly polarized light. Thereby, the layer configuration of the second transmissive optical element 13 can be simplified, and the second transmissive optical element 13 can be composed of one layer, for example.

Figure 2:
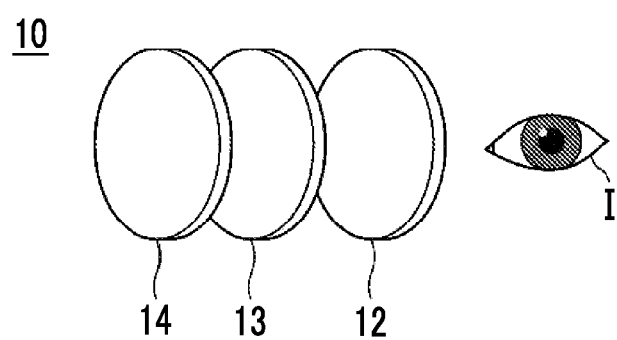
FIG. 2 is a diagram illustrating an example of a configuration of a lens unit.

FIG. 2 is a diagram illustrating a specific configuration of the left and right lens units 10. As shown in FIG. 2, each lens unit 10 comprises a first transmissive optical element 12, a second transmissive optical element 13, and a third optical element 14. The first transmissive optical element 12, the second transmissive optical element 13, and the third optical element 14 are arranged in this order from the eye I side of the wearer. That is, the first transmissive optical element 12 is disposed closer to the wearer than the second transmissive optical element 13.

The first transmissive optical element 12 transmits an image of a subject within the field of view of the wearer and is capable of changing the refractive power. The refractive power of the first transmissive optical element 12 is controlled in accordance with the visual acuity of the wearer. By controlling the refractive power of the first transmissive optical element 12, it is unnecessary to provide a plurality of commodities in accordance with visual acuity of the wearer, and a single product can be compatible with a wide range of users.

As the first transmissive optical element 12, for example, a matrix liquid crystal lens can be used. The matrix liquid crystal lens is divided into a plurality of regions, and is configured such that the refractive index can be changed for each divided region.

By adopting the configuration in which the refractive index can be changed for each divided region as described above, the phase distribution for correcting the abnormality of the wavefront aberration of the eyes of the wearer can be generated. Therefore, not only myopia and hyperopia but also astigmatism and irregular astigmatism may be corrected. The wavefront aberration of the eyes of the wearer is measured in advance by a wavefront aberration sensor or the like, and the phase distribution for correcting the measured wavefront aberration is preset.

As the matrix liquid crystal lens, for example, a liquid crystal lens having two liquid crystal layers whose alignment directions are orthogonal can be used. As the matrix liquid crystal lens, a liquid crystal lens, which have two liquid crystal layers having the same alignment direction and in which a half wave plate is provided between the two liquid crystal layers, may be used. Alternatively, a liquid crystal lens having a plurality of pairs of two liquid crystal layers as described above may be used. By providing a plurality of pairs of two liquid crystal layers in this manner, the variable width of the refractive power can be increased.

In the present embodiment, a liquid crystal lens is used as the first transmissive optical element 12. However, the present invention is not limited to this, and a liquid lens or the like capable of changing the refractive power may be used.

The second transmissive optical element 13 displays an image using an image signal which is output from the imaging unit 3 and makes the image incident on the eye I of the wearer. In the present embodiment, as the second transmissive optical element 13, a phase modulation computer hologram display element forming a volume hologram is used. The phase modulation computer hologram display element is a spatial phase modulator, where a plurality of display pixels are two-dimensionally arranged. The image signal, which is output from the imaging unit 3, is input to a computer hologram generation unit 51 of a control board unit 5 to be described later, and the computer hologram generation unit 51 calculates a computer hologram interference pattern by using the input image signal. Various well-known methods can be used as the method of calculating the computer hologram interference pattern.

The computer hologram interference pattern calculated by the computer hologram generation unit 51 is input to and displayed on the second transmissive optical element 13 which is a phase modulation computer hologram display element. Then, the reference light irradiation unit 4 irradiates the second transmissive optical element 13 with the reference light, whereby the wave front of the display light from the virtual image position is reproduced. As a result, the wearer can observe the reproduced image obtained by using the image captured by the imaging unit 3.

Further, in the related art, it has been known that a three-dimensional image is reproduced by a phase modulation computer hologram display element. However, in the present embodiment, it is not necessary to reproduce a three-dimensional image, and simply it is desired to reproduce a plane image with a depth. Therefore, the above-mentioned first camera 3a and second camera 3b may be ordinary monocular imaging systems. The phase modulation computer hologram display element reproduces the image, which is captured by the first camera 3a and the second camera 3b, as a plane image at a position distant from the phase modulation computer hologram display element. As a result, the amount of calculation for generating the reproduced image in real time can be greatly reduced.

The wearer is able to see stereoscopic view by viewing the reproduced image obtained by using the image captured by the first camera 3a on the right side and the reproduced image obtained by using the image captured by the second camera 3b on the left side with the right eye and the left eye, respectively. Thus it is possible to observe a reproduced image with depth.

Further, in the present embodiment, as described above, the second transmissive optical element 13 is irradiated with the three-color reference light beams in a time division manner. Therefore, the computer hologram generation unit 51 calculates an R component computer hologram interference pattern by using the R component image signal, calculates a G component computer hologram interference pattern by using the G component image signal, and calculates a B component computer hologram interference pattern by using the B component image signal. Then, the second transmissive optical element 13 is controlled so as to display the computer hologram interference pattern of the same color component as the color of the irradiated reference light. As described above, by irradiating the second transmissive optical element 13 with the three-color reference light beams in a time division manner and sequentially displaying the computer hologram interference patterns of three color components in synchronization therewith, more brightly reproduced images can be obtained.

In the present embodiment, as described above, since reproduced images are generated by displaying the computer hologram interference patterns, a loupe system is unnecessary. Therefore, it is possible to reduce the thickness as compared with the case where the image is displayed on the electronic display.

Figure 3A:
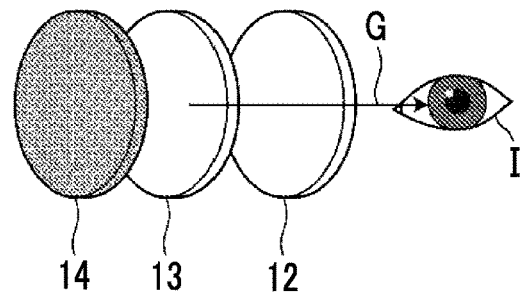
FIG. 3A and FIG. 3B are diagrams for explaining the action of the lens unit.
Figure 3B:
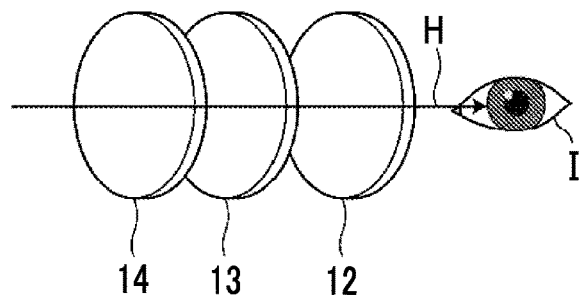

Next, as shown in FIG. 2, the third optical element 14 is disposed closer to the subject side than the above-mentioned second transmissive optical element 13, and is capable of switching between the transmission mode, in which light forming an image of a subject is transmitted, and the blocking mode, in which the light forming the image of the subject is blocked. The third optical element 14 is an electronic dimming barrier, and for example, a liquid crystal display can be used. As shown in FIG. 3A, the third optical element 14 is controlled in the blocking mode in a case where a reproduced image G reproduced by the second transmissive optical element 13 is incident on the eye I of the wearer. In addition, as shown in FIG. 3B, the third optical element 14 is controlled in the transmission mode in a case where an image H of a subject transmitted through the second transmissive optical element 13 is made to be incident on the eye I of the wearer. Further, it is preferable that the third optical element 14 is controlled in the transmission mode in a case where the power supply of the eyeglasses 1 is turned off. Thereby, the wearer is able to use the eyeglasses 1 while wearing it even in a case where the power supply is turned off.

Returning to FIG. 1, the eyeglasses 1 comprises the control board unit 5 and the power supply unit 6. In the present embodiment, the control board unit 5 is provided on the temple 101 on the left side. However, the invention is not limited thereto, and the control board unit 5 may be provided in the temple 101 on the right side. Further, the control board unit 5 may be configured to be attachable to and detachable from the eyeglass body 2.

The power supply unit 6 is attachably and detachably mounted on the distal end (modern) of the temple 101 on the left side. The power supply unit 6 may be a built-in non-rechargeable battery or a built-in rechargeable battery. In addition, electric power may be supplied from an external power supply through a wire, or a wireless power supply system may be used.

Further, it is preferable that the eyeglasses 1 are in a state in which the weight in the horizontal direction is balanced in a case where the wearer wears the eyeglasses 1. The state, in which the weight in the horizontal direction is balanced, means a state in which the position of the center of gravity of the eyeglasses 1 in the horizontal direction is located at the center of the eyeglasses 1 in the horizontal direction.

Therefore, for example, the control board unit 5 and the power supply unit 6 may be provided in the temple 101 on the left side as in the present embodiment. In this case, for example, by providing a weight in the inside of the temple 101 on the right side, the weight in the horizontal direction may be balanced. Further, in order to balance the weight in the horizontal direction, the power supply unit 6 may be provided to be divided into the left and right temples.

Figure 4:
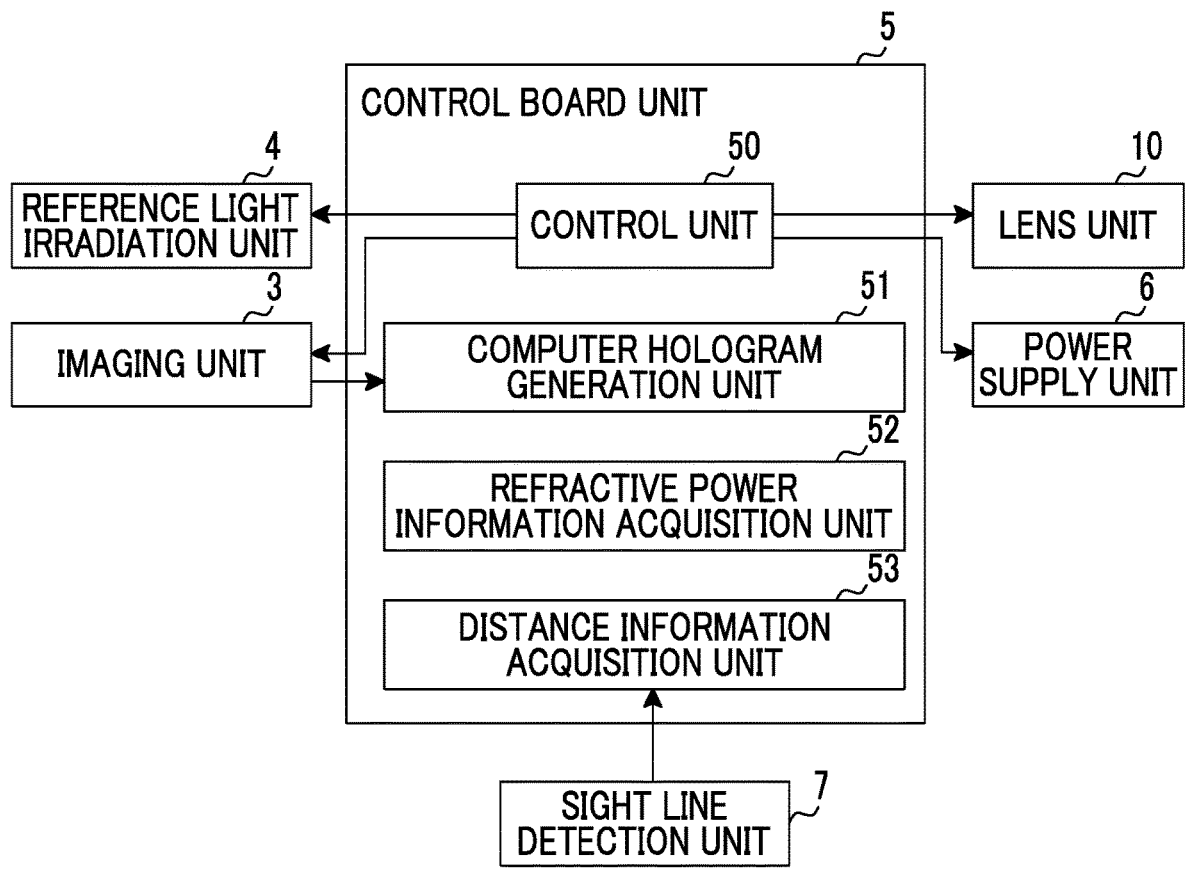
FIG. 4 is a block diagram illustrating an electrical configuration of image displayable eyeglasses according to an embodiment of the present invention.

FIG. 4 is a block diagram illustrating an electrical configuration of the eyeglasses 1. As shown in FIG. 4, the control board unit 5 comprises a control unit 50, a computer hologram generation unit 51, a refractive power information acquisition unit 52, and a distance information acquisition unit 53.

The control board unit 5 comprises a central processing unit (CPU), a memory, and the like, where a control program and a computer hologram generation program, which operate on an operating system (OS) or firmware, are installed therein. The control unit 50, the computer hologram generation unit 51, the refractive power information acquisition unit 52, and the distance information acquisition unit 53 function through the operations of the control program and the computer hologram generation program.

The control unit 50 controls operations of the imaging unit 3, the reference light irradiation unit 4, the lens unit 10, the power supply unit 6, and the sight line detection unit 7.

The computer hologram generation unit 51 generates a computer hologram interference pattern by using the image signal which is output from the imaging unit 3 as described above. The control unit 50 causes the second transmissive optical element 13 to display the computer hologram interference pattern generated by the computer hologram generation unit 51.

The refractive power information acquisition unit 52 acquires the refractive power information of the first transmissive optical element 12. Specifically, the refractive power information acquisition unit 52 acquires information about the refractive power in accordance with the visual acuity of the wearer. For example, information about the refractive power according to conditions of astigmatism, irregular astigmatism, and strabismus and the dioptric power of the eyes of the wearer is acquired.

The refractive power information acquisition unit 52 may acquire information about visual acuity such as astigmatism and the dioptric power of the eyes of the wearer, may obtain the refractive power information of the first transmissive optical element 12 from the information about the visual acuity, and may directly acquire the refractive power information of the first transmissive optical element 12 according to the visual acuity of the wearer.

The information about the visual acuity of the wearer and refractive power information of the first transmissive optical element 12 may be set and input using, for example, an input unit (not shown) provided in the eyeglasses 1. The refractive power information acquisition unit 52 may be set in and input to the external apparatus by communicating with an external apparatus different from the eyeglasses 1 through wireless communication or wire communication. External apparatuses that communicate with the refractive power information acquisition unit 52 include a computer, a mobile terminal, and the like. A dedicated application may be installed, which is for causing the computer and the mobile terminal to display the setting input acceptance screen of the visual acuity of the wearer information and the refractive power information of the first transmissive optical element 12. Further, not only the wireless communication but also the refractive power information may be acquired by connecting the eyeglasses 1 and the computer or the mobile terminal through, for example, a universal serial bus (USB) cable or the like.

The refractive power information of the first transmissive optical element 12 acquired by the refractive power information acquisition unit 52 is output to the control unit 50. The control unit 50 determines the refractive power, which is set for the first transmissive optical element 12, by using the refractive power information and the distance information acquired by the distance information acquisition unit 53, and controls the first transmissive optical element 12.

The distance information acquisition unit 53 acquires information about a distance between the wearer and the subject being viewed by the wearer. In the eyeglasses 1 of the present embodiment, as described above, since the refractive power of the first transmissive optical element 12 is controlled in accordance with the visual acuity of the wearer. Therefore, it is possible to correct myopia, hyperopia, astigmatism, and the like. However, for example, in a case where the wearer is presbyopic, it may be insufficient to adjust the refractive power of the first transmissive optical element 12 in accordance with the dioptric power of the eyes of the wearer in some cases. Therefore, in the present embodiment, the information about the distance between the wearer and the subject is acquired by the distance information acquisition unit 53, and the refractive power of the first transmissive optical element 12 is further adjusted using the information about the distance, thereby performing focus adjustment. Thus, even in a case where the wearer is presbyopic, it is possible to see the image of the subject in focus from a close distance to a long distance.

Specifically, the distance information acquisition unit 53 of the present embodiment acquires information about a sight line direction of the wearer detected by the sight line detection unit 7, and calculates the distance between the wearer and the subject on the basis of the principle of the triangulation method by using the information about the sight line direction.

Specifically, as shown in FIG. 1, the sight line detection unit 7 comprises a first sight line detection unit 7a and a second sight line detection unit 7b. The first sight line detection unit 7a is provided on the upper side of the right rim 102, and the second sight line detection unit 7b is provided on the upper side of the left rim 102. The first sight line detection unit 7a and the second sight line detection unit 7b each comprise: an infrared light source which irradiates the eyes of the wearer with infrared rays; and an infrared camera which captures the reflection image from the crystalline lens and the cornea of the eye due to the irradiation of the infrared rays. In a case where the sight line direction of the wearer is the front direction, the reflection image of the cornea and the reflection image of the crystalline lens coincide in position. However, in a case where the sight line direction is in a direction other than the front direction, the position of the reflection image of the cornea deviates from the position of the reflection image of the crystalline lens. Utilizing this property, the first sight line detection unit 7a calculates the sight line direction of the right eye by using the amount of deviation between the reflection image of the cornea of the right eye and the reflection image of the crystalline lens, and the second sight line detection unit 7b calculates the sight line direction of the left eye by using the amount of deviation between the reflection image of the cornea of the left eye and the reflection image of the crystalline lens.

Then, the sight line directions of the right eye and the left eye calculated by the sight line detection unit 7 are output to the distance information acquisition unit 53. Thereby, as described above, the distance information acquisition unit 53 calculates the distance between the wearer and the subject by using the information about the sight line directions of the right eye and the left eye.

In the present embodiment, the sight line direction of the wearer is detected, and the distance between the wearer and the subject is calculated using the principle of the triangulation method. However, the method of calculating the distance between the wearer and the subject is not limited to this.

For example, the distance between the wearer and the subject may be calculated using contrast information or phase difference information calculated at the time of autofocus control of the first camera 3a and the second camera 3b that capture the subject. Specifically, for example, the distance between the wearer and the subject may be calculated by detecting the lens positions of the first camera 3a or the second camera 3b in a case where the in-focus position is detected using the contrast information or the phase difference information.

Further, the first camera 3a and the second camera 3b are provided at positions separated in the horizontal direction of the eyeglass body 2. Therefore, in a case where the subject is close to the eyeglass body, the distance between the subject image captured by the first camera 3a and the subject image captured by the second camera 3b increases in the horizontal direction. In a case where the subject is far from the eyeglass body, the distance between the subject image captured by the first camera 3a and the subject image captured by the second camera 3b decreases in the horizontal direction. Therefore, the distance between the wearer and the subject may be calculated by calculating the distance between the subject image captured by the first camera 3a and the subject image captured by the second camera 3b.

Further, a convergence angle may be calculated using the sight line directions of the right and left eyes of the wearer, and the distance between the wearer and the subject may be calculated using the convergence angle. It should be noted that the relationship between the convergence angle and the distance may be set in advance by a function, table, or the like.

Further, the amount of movement in the vertical direction of the sight line directions of the right and left eyes of the wearer may be calculated, and the distance between the wearer and the subject may be calculated using the amount of movement. It should be noted that the relationship between the distance and the amount of movement in the vertical direction of the sight line direction may also be set in advance by a function, a table, or the like.

In addition, a myoelectric potential sensor, which measures myoelectric potentials of the right eye and the left eye, may be provided for the eyeglass body 2, a convergence angle may be calculated using the myoelectric potential measured by the myoelectric potential sensor, and the distance between the wearer and the subject may be calculated using the convergence angle. It should be noted that the relationship between the myoelectric potential and the convergence angle is preset. Further, by measuring myoelectric potentials of the right eye and the left eye, the degree of tension of the ciliary body may be calculated, and the distance between the wearer and the subject may be calculated using the degree of tension. In this case as well, the relationship between the myoelectric potential and the degree of tension of the ciliary body and the relationship between the degree of tension and the above-mentioned distance is preset.

Figure 5:
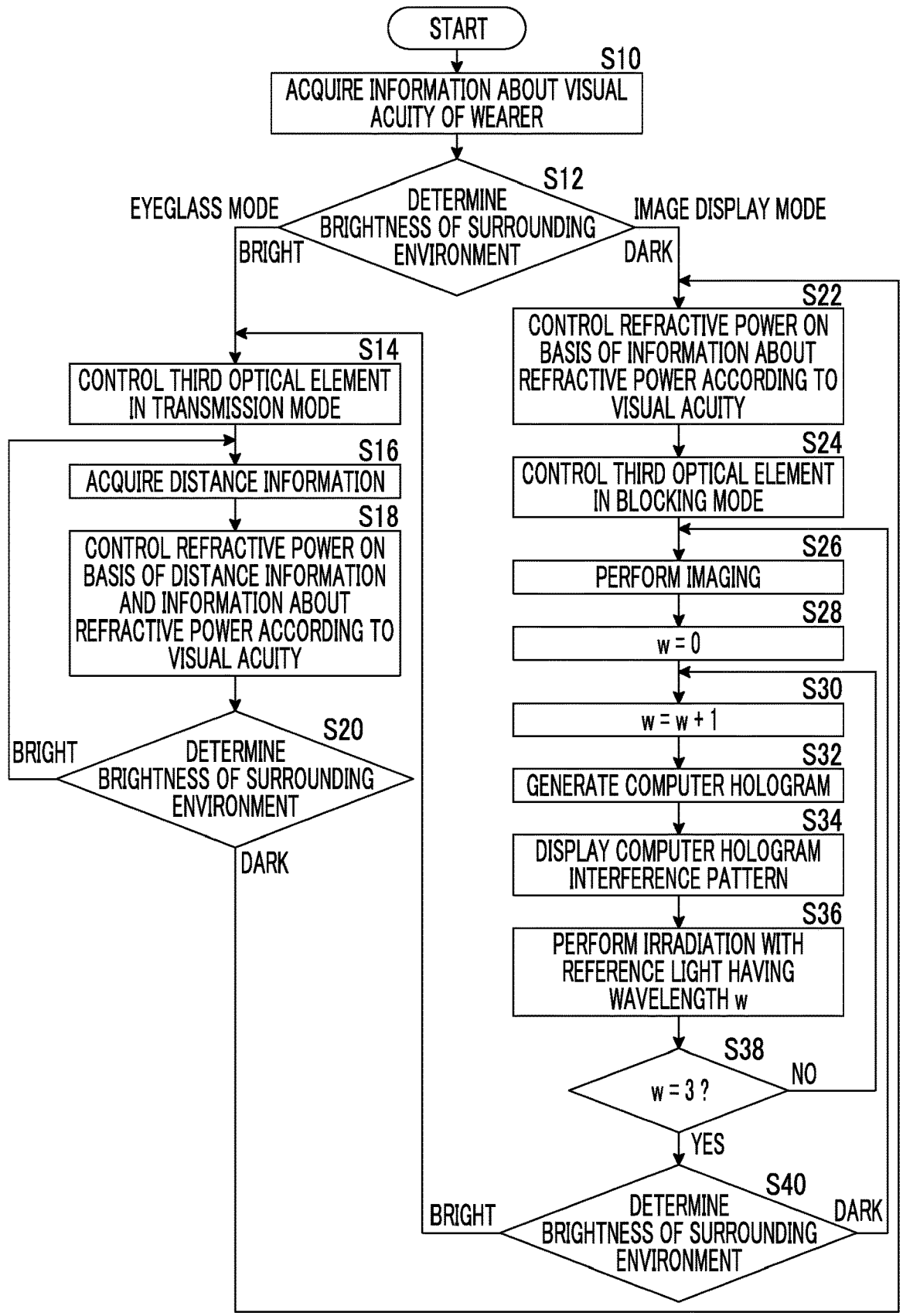
FIG. 5 is a flowchart for explaining the operations of the image displayable eyeglasses according to an embodiment of the present invention.

Next, a series of operations of the eyeglasses 1 of the present embodiment will be described with reference to a flowchart shown in FIG. 5. The eyeglasses 1 of the present embodiment switches between the image display mode and the eyeglass mode in accordance with the brightness of the surrounding environment of the wearer. The image display mode is a mode in which the reproduced image G reproduced by the second transmissive optical element 13 is incident on the eye I of the wearer, and the eyeglass mode is a mode in which the image H of the subject transmitted through the second transmissive optical element 13 is incident on the eye I of the wearer. In a case where the surrounding environment of the wearer is dark, by switching to the image display mode, the wearer is able to see a bright reproduced image G. In a case where the surrounding environment of the wearer is bright, the wearer is able to view a clearer image H of the subject through the eyeglass function.

First, the power button (not shown) of the eyeglasses 1 is pressed, and the power supply of the eyeglasses 1 is turned on. Next, the information about the visual acuity of the wearer is set and input using the input unit, the computer, the mobile terminal, or the like provided in the eyeglasses 1 (S10). The information about the visual acuity of the wearer is acquired by the refractive power information acquisition unit 52, and the refractive power information acquisition unit 52 acquires the refractive power, which is to be set by the first transmissive optical element 12, by using the information about the visual acuity of the wearer. Regarding the information about the visual acuity, for example, the wearer may set and input information measured by a dedicated apparatus. Alternatively, measurement may be performed using an application which is preset in a computer or mobile terminal.

Next, imaging performed by the imaging unit 3 is started, and the image signal acquired by the imaging unit 3 is output to the control unit 50. Then, using the input image signal, the control unit 50 acquires information about the brightness of the surrounding environment of the wearer and determines the brightness of the surrounding environment (S12). Specifically, in a case where the brightness of the surrounding environment is equal to or less than the preset first threshold value, that is, in a case where the surrounding environment is dark, the control unit 50 sets the image display mode. On the other hand, in a case where the brightness of the surrounding environment is greater than the first threshold value, that is, in a case where the surrounding environment is bright, the eyeglass mode is set. As the brightness information of the surrounding environment, statistical values such as an average value, a maximum value, a minimum value, and an intermediate value of the image signal which is output from the imaging unit 3 may be obtained.

Hereinafter, the operations of the eyeglasses 1 in the case of the eyeglass mode will be described. In a case where the eyeglass mode is set, first, the third optical element 14 is controlled in the transmission mode (S14).

Next, the sight line direction of the wearer is detected by the sight line detection unit 7, the information about the sight line direction of the wearer is acquired by the distance information acquisition unit 53, and the distance information acquisition unit 53 acquires the distance to the subject in the sight line direction of the wearer by using the information about the sight line direction (S16).

Then, the control unit 50 acquires the information about the refractive power acquired by the refractive power information acquisition unit 52 and the information about the distance acquired by the distance information acquisition unit 53. The control unit 50 adjusts the refractive power according to the visual acuity of the wearer by using the information about the distance, and controls the first transmissive optical element 12, thereby setting the refractive power as the adjusted refractive power (S18). Thereby, the refractive power of the first transmissive optical element 12 can be set to the refractive power according to the visual acuity of the wearer and the presbyopia state. Therefore, the wearer is able to use the eyeglasses 1 as eyeglasses for near and far vision, and is able to correct astigmatism and irregular astigmatism. In the case of the eyeglass mode, the refractive index of the second transmissive optical element 13 is uniformly controlled.

Figure 6:
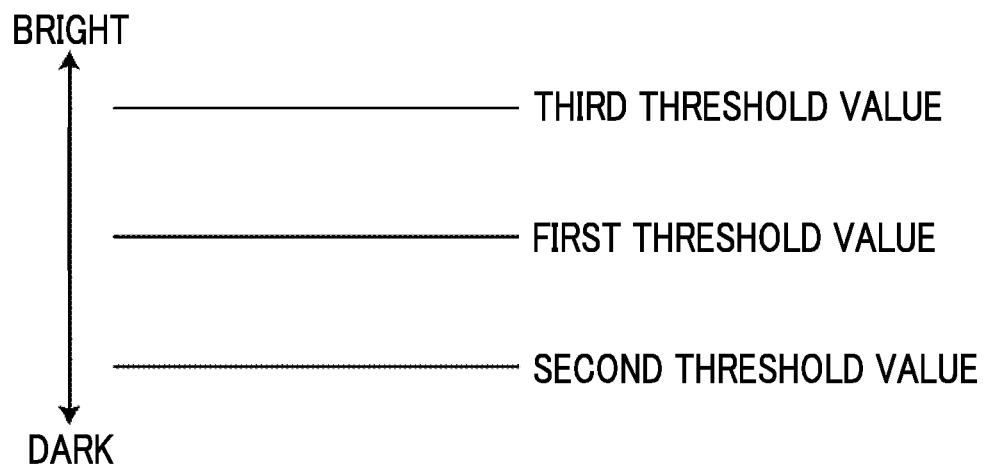
FIG. 6 is a diagram illustrating a relationship of first to third threshold values used for brightness determination of surrounding environment.

After the eyeglass mode is set as described above, the brightness of the surrounding environment is determined at preset intervals (S20). Then, in a case where the brightness of the surrounding environment becomes equal to or less than a preset second threshold value, that is, in a case where the surrounding environment becomes dark, the control unit 50 switches to the image display mode. As shown in FIG. 6, it is desirable that the second threshold value used for the brightness determination at this time is less than the above-mentioned first threshold value. This is because in a case where the second threshold value in S20 is the same as the first threshold value in S12, the eyeglass mode and the image display mode are switched due to a slight difference in brightness of the surrounding environment, which is troublesome for the wearer.

Next, the operations of the eyeglasses 1 in the image display mode will be described. As described above, in the case where the surrounding environment is determined to be dark in S20 after entering the eyeglass mode, and in the case where it is determined that the brightness of the surrounding environment is less than the first threshold value in the initial state of S12, the image display mode is set.

In the image display mode, first, the control unit 50 acquires the information about the refractive power acquired by the refractive power information acquisition unit 52. The control unit 50 controls the first transmissive optical element 12 by using the refractive power information, and sets the refractive power in accordance with the visual acuity of the wearer (S22). In the eyeglasses 1 of the present embodiment, the first transmissive optical element 12 is disposed closer to the wearer than the second transmissive optical element 13. Therefore, the refractive power of the first transmissive optical element 12 is set in accordance with the visual acuity of the wearer. Thereby, it is possible to adjust the position of the reproduced image. As a result, the wearer is able to clearly see the reproduced image reproduced by the second transmissive optical element 13. In a case where the wearer is myopic, the position of the reproduced image is preferably closer to the subject than the second transmissive optical element 13. In a case where the wearer is hyperopic or presbyopic, the position of the reproduced image is preferably closer to the wearer than the second transmissive optical element 13.

Subsequently, the control unit 50 controls the third optical element 14 in the blocking mode (S24). Thereby, it is possible to prevent external light from being incident on the eyes of the wearer. Then, the imaging unit 3 captures an image within the field of view of the wearer (S26), and the image signal, which is output from the imaging unit 3, is input to the computer hologram generation unit 51.

Then, under the control of the control unit 50, the reference light irradiation unit 4 irradiates the second transmissive optical element 13 with reference light beams of three colors of green (G), blue (B), and red (R) in this order in a time division manner. Specifically, the irradiation of the three-color reference light beams is controlled as follows. First, the wavelength number w indicating the wavelength (color) of the reference light is set to zero (S28). In the present embodiment, the wavelength number w of the G reference light is set to "1", the wavelength number w of the B reference light is set to "2", and the wavelength number w of the R reference light is set to "3".

Then, the wavelength number w is incremented by "1", and the wavelength number w is set to "1". In a case where the wavelength number w is set to "1", the computer hologram generation unit 51 generates a computer hologram interference pattern of the G component by using the input image signal (S32), and the pattern is displayed on the second transmissive optical element 13 (S34). At this time, the second transmissive optical element 13 is irradiated with the reference light having a wavelength (color) corresponding to the wavelength number. That is, the second transmissive optical element 13 is irradiated with the G reference light having the wavelength number w of "1" (S36). As a result, the reproduced image of the G component is first incident on the eyes of the wearer.

Then, the control unit 50 confirms whether or not the current wavelength number w is "3" (S38). In a case where the wavelength number w is not "3", the process returns to S30, the wavelength number w is incremented by "1", and the wavelength number w is set to "2".

In a case where the wavelength number w is set to "2", the computer hologram generation unit 51 generates a computer hologram interference pattern of the B component by using the input image signal (S32), and the pattern is displayed on the second transmissive optical element 13 (S34). At this time, the second transmissive optical element 13 is irradiated with the B reference light having the wavelength number w of "2" (S36). As a result, the reproduced image of the B component is incident on the eyes of the wearer.

Then, the control unit 50 confirms again whether or not the current wavelength number w is "3" (S38). In a case where the wavelength number w is not "3", the process returns to S30, the wavelength number w is incremented by "1", and the wavelength number w is set to "3".

In a case where the wavelength number w is set to "3", the computer hologram generation unit 51 generates a computer hologram interference pattern of the R component by using the input image signal (S32), and the pattern is displayed on the second transmissive optical element 13 (S34). At this time, the second transmissive optical element 13 is irradiated with the R reference light having the wavelength number w of "3" (S36). As a result, the reproduced image of the R component is incident on the eyes of the wearer.

By repeating the irradiation of the reference light of the color corresponding to the wavelength number w and the display of the computer hologram interference pattern while incrementing the wavelength number w as described above, the reproduced images are made to be incident on the eyes of the wearer in the order of the G component, the B component, and the R component. The reason why the reproduced image is made to be incident in such an order is as follows. The G component among the three color components has the highest luminosity factor, and it is preferable that light having the G component is made to be preferentially incident in order to use the time lag. In addition, the B component has a high luminosity factor in a case where the eyes are adapting to the dark, and thus it is preferable that the light having the B component is made to be incident second.

In the image display mode, each time the image signal of one frame is output from the imaging unit 3, the processing from S28 to S38 is repeated. Even after the image display mode is set as described above, the brightness of the surrounding environment is determined at preset intervals (S40). Then, in a case where the brightness of the surrounding environment becomes greater than a preset third threshold value, that is, in a case where the surrounding environment becomes bright, the control unit 50 switches to the eyeglass mode. As shown in FIG. 6, it is desirable that the third threshold value used for the brightness determination at this time is greater than the above-mentioned first threshold value. This is because in a case where the third threshold value in S40 is the same as the first threshold value in S12, the eyeglass mode and the image display mode are switched due to a slight difference in brightness of the surrounding environment, which is troublesome for the wearer.

In the eyeglasses 1 of the above embodiment, in a case where the brightness of the surrounding environment is between the first threshold value and the second threshold value and in a case where the brightness is between the first threshold value and the third threshold value, the control unit 50 may set the intermediate mode. In the intermediate mode, the reproduced image is displayed by the second transmissive optical element 13, and the image of the subject transmitted through the first transmissive optical element 12 and the second transmissive optical element 13 may be made to be incident on the eyes of the wearer. Further, in the case of the intermediate mode, the transmittance of the light forming the image of the subject through the third optical element 14 may be changed continuously or stepwise.

Further, in a case where the above-mentioned intermediate mode is not set, the image display mode and the eyeglass mode may be switched using only the first threshold value without setting the second threshold value and the third threshold value.

Further, in the eyeglasses 1 of the present embodiment, as described above, the eyeglass mode and the image display mode are switched using the result of the brightness determination, but the first threshold value used for the brightness determination may be changed depending on whether the wearer is in the room or the wearer is outside. Specifically, for example, in a case where the wearer is in the room, switching between the eyeglass mode and the image display mode may be performed depending on whether or not the brightness is suitable for work of visual display terminals (VDT). Generally, it is desirable that the surrounding environment has a brightness of 300 to 500 lux or more in order to perform the VDT work. Therefore, in a case where the wearer is in the room, it is desirable to set the first threshold value used for the brightness determination to a value corresponding to 300 to 500 lux. The second and third threshold values may be appropriately set in accordance with the first threshold value.

On the other hand, in a case where the wearer is outside, switching between the eyeglass mode and the image display mode may be performed depending on whether or not the brightness is enough for the wearer to walk safely. Generally, in order to walk safely outside, it is necessary to have a brightness of about a moonlight level, and it is desirable that the surrounding environment has a brightness of 0.1 to 1 lux or more. Therefore, in a case where the wearer is outside, it is desirable to set the first threshold value used for the brightness determination to a value corresponding to 0.1 to 1 lux. In addition, in a case where the wearer is an elderly person, it is desirable to have the brightness of about a street lamp level in order to walk outside safely, and it is desirable that the surrounding environment has a brightness of 50 to 200 lux or more. Therefore, in a case where the wearer is an elderly person and is outside, it is desirable to set the first threshold value used for the brightness determination to a value corresponding to 50 to 200 lux.

It should be noted that the switching of the first to third threshold values described above may be performed using an input unit (not shown) provided in the eyeglasses 1, for example, or may be performed using a computer or a mobile terminal communicating with the eyeglasses 1. Alternatively, it may be automatically determined whether the wearer is in the room or outside by using the image signal captured by the imaging unit 3, and switching of the first to third threshold values may be performed in accordance with the determination result.

Figure 7:
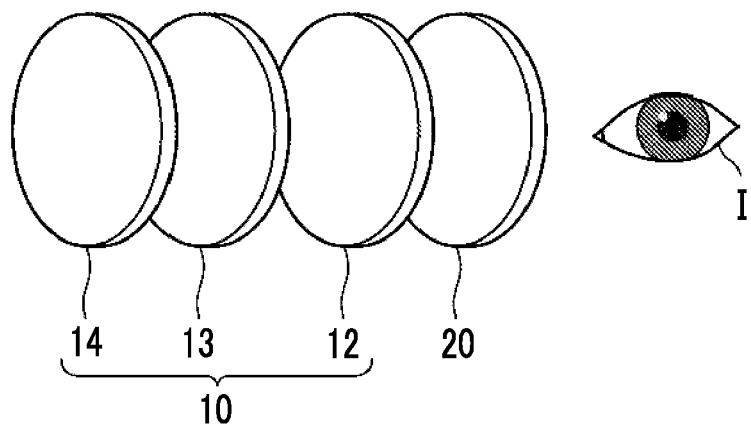
FIG. 7 is a diagram illustrating a fixed focal length lens attachable to and detachable from a lens unit.

Further, in the eyeglasses 1 of the above embodiment, as shown in FIG. 7, the fixed focal length lens 20 may be provided on a side close to the wearer in the lens unit 10, and it is desirable that a plurality of fixed focal length lenses 20 having different refractive powers are configured to be interchangeable in the eyeglass body 2. By providing the fixed focal length lens 20 suitable for the visual acuity of the wearer, it is possible to suppress the variable width of the refractive power of the first transmissive optical element 12 and the variable width of the position of the reproduced image reproduced by the second transmissive optical element 13. As a result, the load on these optical elements can be reduced. It should be noted that various well-known configurations can be used as the mechanical configuration in which the fixed focal length lens 20 is interchangeable.

Further, in the eyeglasses 1 of the above embodiment, in a case where the power supply is turned off, it is desirable to control the refractive indices of the first transmissive optical element 12 and the second transmissive optical element 13 uniformly. As a result, it is possible to prevent darkening and scattering in a case where the power supply is turned off.

Further, in the eyeglasses 1 of the above embodiment, it is preferable that the imaging unit 3 has a zooming function. Enlarged images and images having a wider angle than that of normal vision can be obtained as necessary. Such a zooming function is realized by the imaging unit 3 having a zoom lens or having a digital zoom function. For changing the magnification of the imaging unit 3, setting may be input using the input unit provided in the eyeglasses 1, or may be input in the computer and the mobile terminal communicating with the eyeglasses 1.

In the eyeglasses 1 of the above embodiment, in the case of the image display mode, the third optical element 14 is controlled in the blocking mode. However, the present invention is not limited to this, and the third optical element 14 may be controlled in a semi-transmission mode for blocking a part of the light forming the image of the subject.

Figure 8:
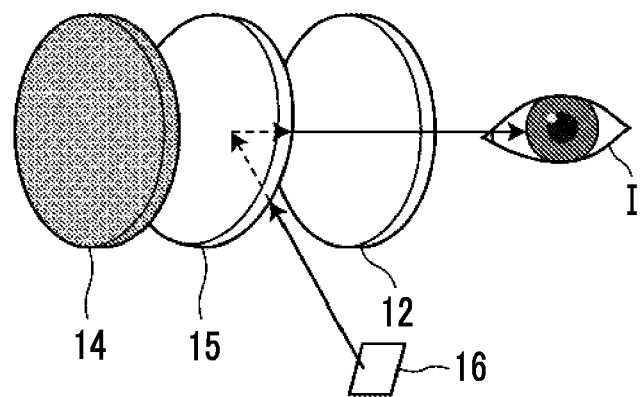
FIG. 8 is a diagram illustrating another embodiment of a second transmissive optical element.

Further, in the eyeglasses 1 of the above embodiment, the phase modulation computer hologram display element is used as the second transmissive optical element 13. However, the present invention is not limited to this, and as shown in FIG. 8, a free-form surface semi-transmissive mirror or a holographic optical element may be used as the second transmissive optical element 15. Then, the image captured by the imaging unit 3 is displayed on the display element 16, and the image displayed on the display element 16 is reflected in the direction of the eye I of the wearer by the second transmissive optical element 15. Thereby, a virtual image may be provided to the wearer.

The free-form surface semi-transmissive mirror and the holographic optical element may employ a free-form surface semi-transmissive mirror capable of transmitting the image of the subject transmitted through the third optical element 14 and capable of reflecting the image displayed on the display element 16. This is advantage for mass production. In addition, in a case of using the holographic optical element, by providing wavelength selectivity, it may be efficient that both the reflectance of the display wavelength of the image displayed on the display element 16 and the transmittance of light other than the display wavelength are set to 50% or more.

Further, the display element 16 may be provided, for example, on each rim 102 of the eyeglass body 2. It is desirable that the display element 16 is provided on the lower side of each of the left and right rims 102. With such a configuration, the display element 16 can be prevented from entering the field of view of the wearer, and can be disposed between the wearer's face and the rim 102, such that the display element 16 does not become an obstacle. As the display element, for example, a liquid crystal display and an organic electro luminescence (EL) display or the like can be used.

Figure 9:
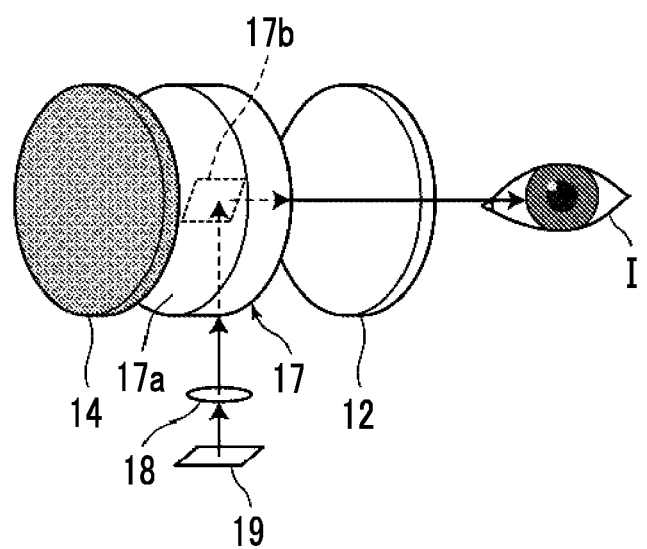
FIG. 9 is a diagram illustrating another embodiment of the second transmissive optical element.

Further, the configuration, which is for reflecting the image displayed on the display element by the second transmissive optical element and making the image incident on the eye I of the wearer, is not limited to the configuration shown in FIG. 8. For example, as shown in FIG. 9, the second transmissive optical element 17 may be configured such that a semi-transmissive reflection unit 17b consisting of a free-form surface semi-transmissive mirror or a holographic optical element or the like is provided at the center of a light guide plate 17a. Then, the image displayed on the display element 19 may be made to be incident on the light guide plate 17a through the lens 18, and the image guided by the light guide plate 17a may reflected by the semi-transmissive reflection unit 17b so as to be incident on the eye I of the wearer.

Figure 10:
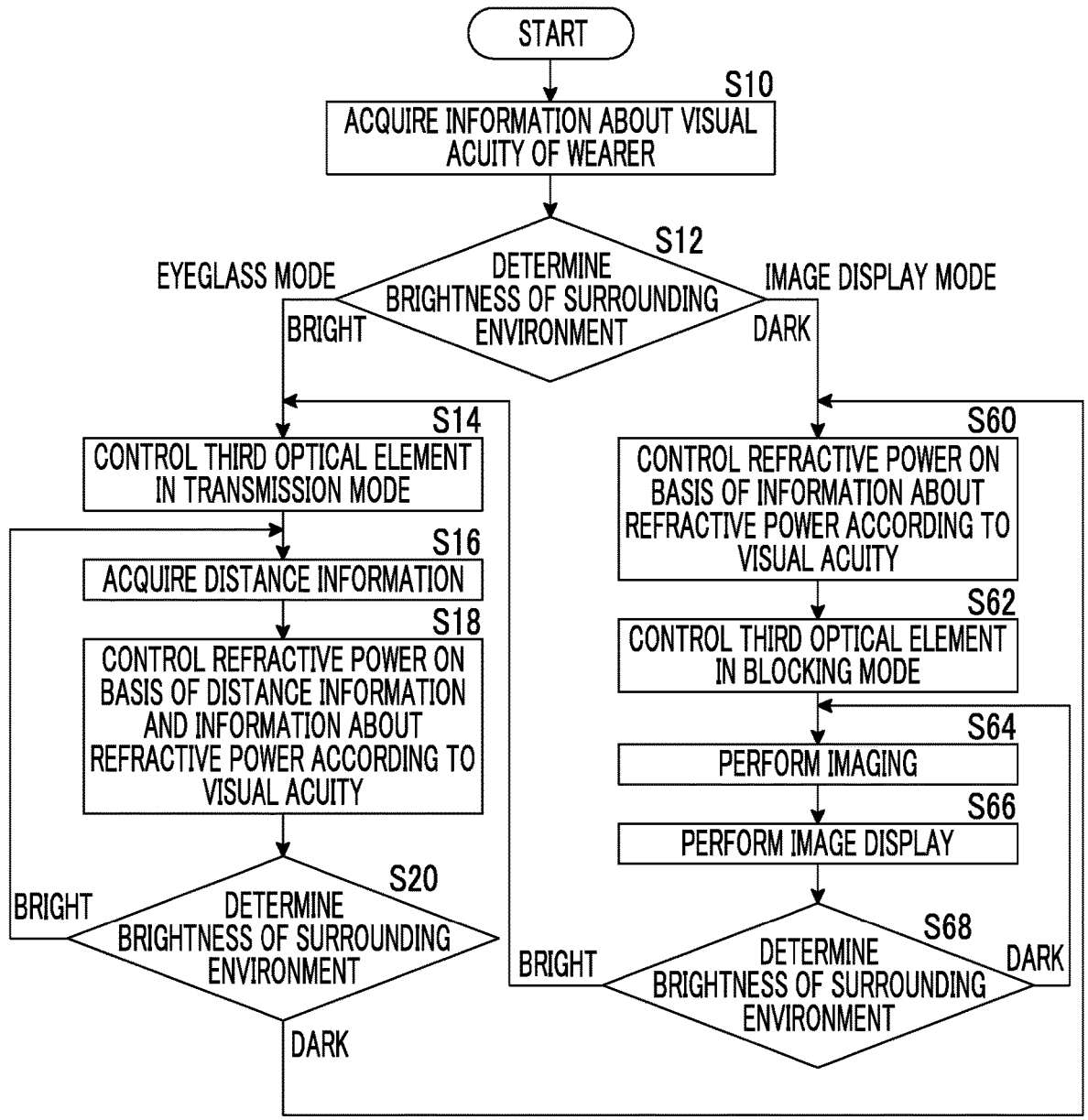
FIG. 10 is a flowchart for explaining the operations of the image displayable eyeglasses in a case of the configuration shown in FIGS. 8 and 9.

Next, operations of the eyeglasses 1 in a case where the lens unit 10 is configured as shown in FIGS. 8 and 9 will be described with reference to a flowchart shown in FIG. 10. It should be noted that the operations in the eyeglass mode in S10, S12, and S14 to S20 are similar to those in the above embodiment, and thus only the operations in the image display mode will be described herein.

As in the above-mentioned embodiment, in a case where it is determined that the brightness of the surrounding environment is greater than the first threshold value in S12, and in a case where it is determined that the surrounding environment is dark in S20 after entering the eyeglass mode, the image display mode is set.

In the image display mode, first, the control unit 50 acquires the information about the refractive power acquired by the refractive power information acquisition unit 52. The control unit 50 controls the first transmissive optical element 12 using the refractive power information to set the refractive power in accordance with the visual acuity of the wearer (S60).

Subsequently, the control unit 50 controls the third optical element 14 in the blocking mode (S62). Thereby, it is possible to prevent external light from being incident on the eyes of the wearer. Then, the imaging unit 3 captures an image within the field of view of the wearer (S64), and the image signal, which is output from the imaging unit 3, is input to the display elements 16 and 19 to display an image (S66). The images displayed on the display elements 16 and 19 are reflected by the second transmissive optical elements 15 and 17, and are incident on the eyes of the wearer.

Even after the image display mode is set as described above, the brightness of the surrounding environment is determined at preset intervals (S68). Then, in a case where the brightness of the surrounding environment becomes greater than a preset third threshold value, that is, in a case where the surrounding environment becomes bright, the control unit 50 switches to the eyeglass mode. The third threshold value used for the brightness determination at this time is the same as in the above embodiment.

Figure 11:
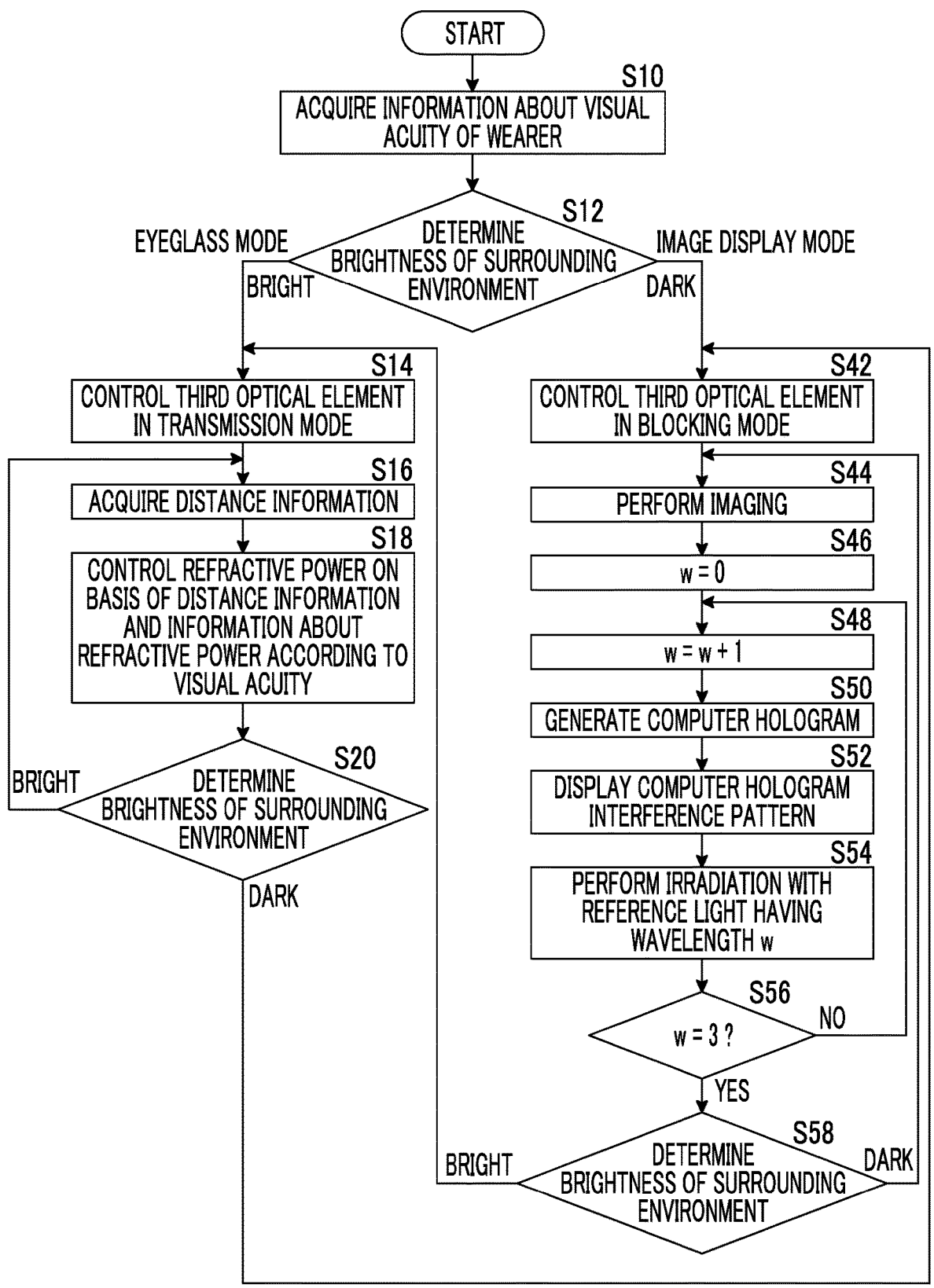
FIG. 11 is a flowchart for explaining the operations of the image displayable eyeglasses in a case where the second transmissive optical element is made to function as a first transmissive optical element.

Further, by making the second transmissive optical element 13 in the above embodiment function as the first transmissive optical element 12, the first transmissive optical element 12 may be omitted. In this case, by controlling the refractive index of each pixel of the phase modulation computer hologram display element as the second transmissive optical element 13, the second transmissive optical element 13 may be made to function as a matrix liquid crystal lens. FIG. 11 is a flowchart showing the flow of the operations of the eyeglasses 1 in a case where the second transmissive optical element 13 is made to function as the first transmissive optical element as described above. As shown in FIG. 11, operations of the eyeglass mode in S10, S12, and S14 to S20 are the same as those of the above embodiment, and operations of the image display mode shown in S42 to S56 are different from those of the above embodiment. Specifically, since the first transmissive optical element 12 is omitted, the refractive power of the first transmissive optical element 12 in S22 shown in FIG. 5 is not controlled. The other processes in S42 to S58 shown in FIG. 11 are the same as the processes from S24 to S40 shown in FIG. 5.

Further, as the second transmissive optical element 13 of the above embodiment, a thin hologram element forming a two-dimensional refractive index distribution may be used. The thin hologram element is composed of a two-dimensional matrix liquid crystal. Compared with a volume hologram, the thin hologram element can be configured to have a simple structure. However, the thin hologram element functions as a transmissive hologram. Therefore, it is desirable to provide a wavelength selective reflection member on the subject side surface of the thin hologram element in order to sufficiently reflect the above-mentioned reference light. The wavelength selective reflection member reflects the reference light, and transmits light having a wavelength other than that of the reference light. Since the bandwidth of each of the G, B, and R reference light beams is narrow, the wavelength selective reflection member is able to transmit the image of the subject by transmitting light having a wavelength other than that of the reference light.

In the above-mentioned embodiment, the second transmissive optical element 13 is irradiated with the G, B, and R reference light beams in a time division manner. However, the second transmissive optical element 13 may be irradiated with the G, B, and R reference light beams at the same time. In this case, the second transmissive optical element 13 displays the computer hologram interference pattern obtained by simulating multiple exposures of three-type reference light beams of G, B, and R. A well-known method can be used for generating the computer hologram interference pattern obtained by simulating multiple exposures (for example, refer to "Holograph Using Commercial Film", Production Research, Vol. 18, No. 9, 1966.09.01, pp. 237-242). By simultaneously performing irradiation with the G, B, and R reference light beams, the frame rate can be increased.

Figure 12A:
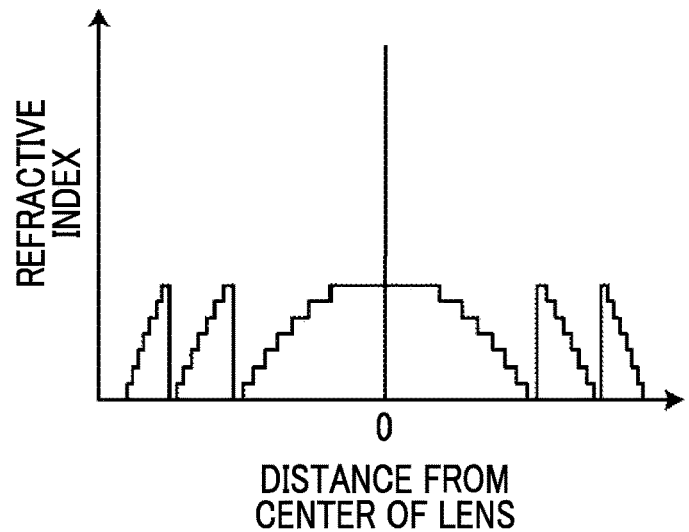
FIGS. 12A to 12C are diagrams illustrating an example of refractive index distribution of the first transmissive optical element.
Figure 12B:
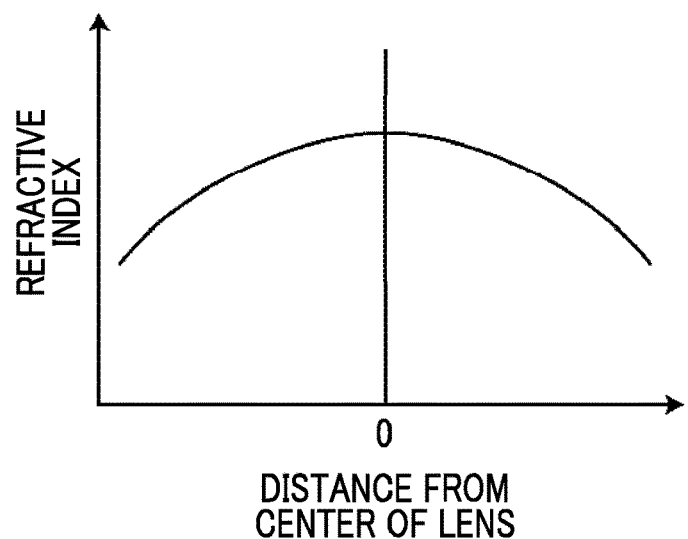
Figure 12C:
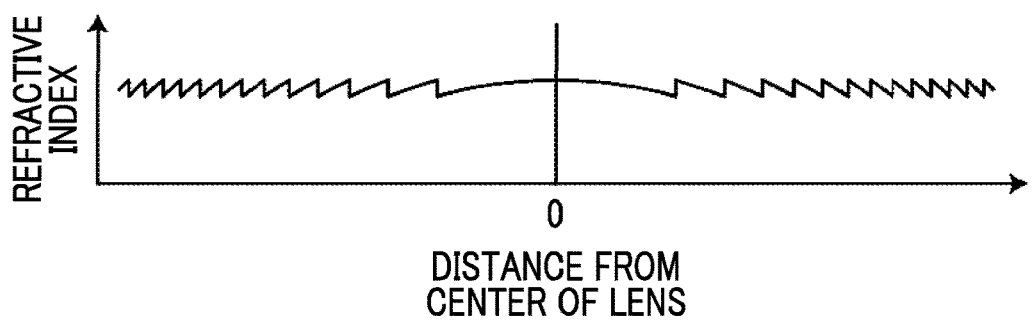

Further, in the eyeglasses 1 of the above-mentioned embodiment, it is desirable that the first transmissive optical element 12 is formed as a lens centering on a position corresponding to the sight line. Specifically, for example, as shown in FIG. 12A, it is desirable that the Fresnel type refractive index distribution is set such that the first transmissive optical element 12 functions as a diffraction type lens. Furthermore, as shown in FIG. 12B, the refractive index distribution continuous from the center of the lens may be set such that the first transmissive optical element 12 functions as a refractive lens. Further, the refractive index distribution as shown in FIG. 12C may be set such that the first transmissive optical element 12 functions as a Fresnel lens. In addition, even in a case of setting the refractive index distribution as shown in FIGS. 12A to 12C, the refractive power of the first transmissive optical element 12 is further controlled by using the information about the visual acuity of the wearer and the distance between the wearer and the subject.

In the above embodiment, the information about the brightness of the surrounding environment of the wearer is acquired using the image signal which is output from the imaging unit 3. However, the present invention is not limited to this, and a brightness detection unit other than the imaging unit 3 may be provided. As the brightness detection unit, for example, a photo detector (PD) such as a photodiode may be used.

In the above embodiment, the image using the image signal, which is output from the imaging unit 3, is displayed or reflected by the second transmissive optical element. However, the image signal, which is output from the imaging unit 3, does not have to be used. For example, the control unit 50 may be configured to communicate with an external apparatus different from the eyeglasses 1, acquire an image signal which is output from the external apparatus, and display or reflect the image using the image signal through the second transmissive optical element.

Further, in the eyeglasses 1 of the present embodiment, a wearing state detection unit, which detects a state in the wearer wears the eyeglasses 1 is provided, and may automatically turn on the power supply in a case where the wearer wears the eyeglasses 1, and may automatically turn off the power supply in a case where the wearer removes the eyeglasses 1. The wearing state detection unit is able to detect the wearing state of the eyeglass body 2 on the wearer, for example, by detecting the opening/closing state of the temple 101 through the open/close sensor. As the open/close sensor, for example, it is possible to use a limit switch, which is turned on in a state where the temple 101 is closed and turned off in a state where the temple 101 is opened, or the like.

Further, the method of detecting the wearing state of the eyeglass body 2 on the wearer is not limited to the above-mentioned method. For example, a close contact sensor may be provided on a portion of the ear of the temple 101 or the nose pad 104 of the eyeglass body 2. The close contact sensor may be configured to detect the wearing state of the eyeglass body 2 on the wearer by detecting the close contact with the skin. As the close contact sensor, for example, a pressure sensor that outputs a signal corresponding to the pressure can be used.

EXPLANATION OF REFERENCES

1: eyeglasses
2: eyeglass body

3: imaging unit
3a: first camera
3b: second camera
4: reference light irradiation unit
4a: first light source unit
4b: second light source unit
5: control board unit
6: power supply unit
7: sight line detection unit
7a: first sight line detection unit
7b: second sight line detection unit
10: lens unit
11: frame
12: first transmissive optical element
13: second transmissive optical element
14: third optical element
15, 17: transmissive optical element
16, 19: display element
17a: light guide plate
17b: semi-transmissive reflection unit
18: lens
20: fixed focal length lens
50: control unit
51: computer hologram generation unit
52: refractive power information acquisition unit
52: distance information acquisition unit
53: distance information acquisition unit
101: temple
102: rim
103: bridge
104: nose pad
G: reproduced image
H: image
I: eye

What is claimed is:

1. Image displayable eyeglasses comprising:
an eyeglass body;
a first transmissive optical element that transmits an image of a subject and is capable of changing a refractive power;
a second transmissive optical element that displays or reflects an image using an image signal and transmits the image of the subject; and
a processor that performs control capable of switching between an image display mode, in which the image is displayed or reflected by the second transmissive optical element so as to be incident on eyes of a wearer of the eyeglass body, and an eyeglass mode, in which the image of the subject transmitted through the first transmissive optical element and the second transmissive optical element is incident on the eyes of the wearer,
wherein the first transmissive optical element is disposed closer to the wearer than the second transmissive optical element,
wherein the processor controls a refractive index of the second transmissive optical element uniformly in the case of the eyeglass mode,
wherein the processor acquires information about a brightness of surrounding environment of the wearer and switches from the eyeglass mode to the image display mode in a case where the brightness is equal to or less than a preset first threshold value,
wherein the processor performs switching from the eyeglass mode to the image display mode in a case where the brightness is changed to equal to or less than a second threshold value smaller than the first threshold value in a state where the brightness is greater than the first threshold value and the eyeglass mode is set, and performs switching from the image display mode to the eyeglass mode in a case where the brightness is changed to greater than a third threshold value greater than the first threshold value in a state where the brightness is equal to or less than the first threshold and the image display mode is set.

2. The image displayable eyeglasses according to claim 1, wherein the first transmissive optical element is a liquid crystal lens.

3. The image displayable eyeglasses according to claim 1, further comprising
a third optical element that is disposed closer to the subject than the second transmissive optical element and is capable of switching between a transmission mode, in which light forming the image of the subject is transmitted, and a blocking mode, in which the light forming the image of the subject is blocked,
wherein the processor controls the third optical element such that the third optical element is set in the blocking mode in a case of the image display mode and controls the third optical element such that the third optical element is set in the transmission mode in a case of the eyeglass mode.

4. The image displayable eyeglasses according to claim 1, further comprising
a third optical element that is disposed closer to the subject than the second transmissive optical element and is capable of switching between a transmission mode, in which light forming the image of the subject is transmitted, and a semi-transmission mode, in which a part of the light forming the image of the subject is blocked,
wherein the processor controls the third optical element such that the third optical element is set in the semi-transmission mode in a case of the image display mode and controls the third optical element such that the third optical element is set in the transmission mode in a case of the eyeglass mode.

5. The image displayable eyeglasses according to claim 1, wherein the processor further acquires refractive power information of the first transmissive optical element and controls the refractive power of the first transmissive optical element by using the refractive power information.

6. The image displayable eyeglasses according to claim 1, wherein a plurality of fixed focal length lenses having different refractive powers are configured to be interchangeable on a side close to the wearer in the first transmissive optical element.

7. The image displayable eyeglasses according to claim 1, wherein the processor further acquires information about a distance between the wearer and the subject and controls a refractive power of the first transmissive optical element by using the information about the distance.

8. The image displayable eyeglasses according to claim 1, wherein the processor uniformly controls refractive indices of the first transmissive optical element and the second transmissive optical element in a case where a power supply is turned off.

9. The image displayable eyeglasses according to claim 1, wherein the first transmissive optical element has two liquid crystal layers whose alignment directions are orthogonal to each other.

10. The image displayable eyeglasses according to claim 1, wherein the first transmissive optical element has two liquid crystal layers having the same alignment direction, and a half wave plate is provided between the two liquid crystal layers.

11. The image displayable eyeglasses according to claim 1, wherein the processor controls the first transmissive optical element such that the first transmissive optical element generates a phase distribution for correcting abnormality of wavefront aberration of each eye.

12. The image displayable eyeglasses according to claim 1, further comprising an imaging unit that captures the image of the subject and outputs the image signal.

13. The image displayable eyeglasses according to claim 1, wherein the processor changes a transmittance of the light forming the image of the subject through the third optical element continuously or stepwise in a case where the brightness is between the first threshold value and the second threshold value and in a case where the brightness is between the first threshold value and the third threshold.

14. The image displayable eyeglasses according to claim 13, wherein the processor performs control in an intermediate mode, in which the image is displayed by the second transmissive optical element and the image of the subject transmitted through the first transmissive optical element and the second transmissive optical element is made to be incident on the eyes of the wearer, in a case where the brightness is between the first threshold value and the second threshold value and in a case where the brightness is between the first threshold value and the third threshold value.

15. Image displayable eyeglasses comprising:
an eyeglass body;
a transmissive optical element that transmits an image of a subject, is capable of changing a refractive power, and displays an image using an image signal; and
a processor that performs control capable of switching between an image display mode, in which the image is displayed by the transmissive optical element so as to be incident on eyes of a wearer of the eyeglass body, and an eyeglass mode, in which the image of the subject transmitted through the transmissive optical element is incident on the eyes of the wearer,
wherein the processor acquires information about a brightness of surrounding environment of the wearer and switches from the eyeglass mode to the image display mode in a case where the brightness is equal to or less than a preset first threshold value,
wherein the processor performs switching from the eyeglass mode to the image display mode in a case where the brightness is changed to equal to or less than a second threshold value smaller than the first threshold value in a state where the brightness is greater than the first threshold value and the eyeglass mode is set, and performs switching from the image display mode to the eyeglass mode in a case where the brightness is changed to greater than a third threshold value greater than the first threshold value in a state where the brightness is equal to or less than the first threshold and the image display mode is set.

16. Image displayable eyeglasses comprising:
an eyeglass body;
a first transmissive optical element that transmits an image of a subject and is capable of changing a refractive power;
a second transmissive optical element that displays or reflects an image using an image signal and transmits the image of the subject; and
a control unit processor that performs control capable of switching between an image display mode, in which the image is displayed or reflected by the second transmissive optical element so as to be incident on eyes of a wearer of the eyeglass body, and an eyeglass mode, in which the image of the subject transmitted through the first transmissive optical element and the second transmissive optical element is incident on the eyes of the wearer,
wherein the first transmissive optical element is disposed closer to the wearer than the second transmissive optical element,
wherein the second transmissive optical element is a phase modulation computer hologram display element,
wherein the phase modulation computer hologram display element displays a computer hologram interference pattern using the image signal.

17. The image displayable eyeglasses according to claim 16, wherein the phase modulation computer hologram display element has a plurality of display pixels.

18. The image displayable eyeglasses according to claim 16, wherein the phase modulation computer hologram display element reproduces the image as a plane image at a position distant from the phase modulation computer hologram display element.

19. The image displayable eyeglasses according to claim 16, further comprising a reference light irradiation unit that irradiates the phase modulation computer hologram display element with reference light.

20. The image displayable eyeglasses according to claim 19, wherein the phase modulation computer hologram display element is a thin hologram element.

* * * * *